(12) United States Patent
Mendonça et al.

(10) Patent No.: US 9,036,879 B2
(45) Date of Patent: May 19, 2015

(54) MULTI-MATERIAL DECOMPOSITION USING DUAL ENERGY COMPUTED TOMOGRAPHY

(75) Inventors: Paulo Ricardo dos Santos Mendonça, Clifton Park, NY (US); Paul Edgar Licato, Wauwatosa, WI (US); Rahul Bhotika, Albany, NY (US); Brian William Thomsen, Milwaukee, WI (US)

(73) Assignee: General Electric Company, Niskayuna, NY (US)

( * ) Notice: Subject to any disclaimer, the term of this patent is extended or adjusted under 35 U.S.C. 154(b) by 842 days.

(21) Appl. No.: 12/315,184

(22) Filed: Nov. 28, 2008

(65) Prior Publication Data

US 2010/0135453 A1    Jun. 3, 2010

(51) Int. Cl.
 *G06K 9/00* (2006.01)
 *A61B 6/00* (2006.01)
 *A61B 6/03* (2006.01)

(52) U.S. Cl.
 CPC .............. *A61B 6/4241* (2013.01); *A61B 6/032* (2013.01); *A61B 6/482* (2013.01); *Y10S 378/901* (2013.01)

(58) Field of Classification Search
 CPC ...... A61B 6/4241; A61B 6/032; A61B 6/482; A61B 6/03; A61B 6/48; A61B 6/42
 USPC ........ 382/128–134; 250/208.1, 214 R, 214.1, 250/559.4, 370.08, 370.09; 378/4, 5, 6, 18, 378/54, 56, 86, 207, 901, 98.9, 98.11, 98.12
 See application file for complete search history.

(56) References Cited

U.S. PATENT DOCUMENTS

| | | | |
|---|---|---|---|
| 5,155,365 A * | 10/1992 | Cann et al. | 250/363.02 |
| 6,950,493 B2 * | 9/2005 | Besson | 378/16 |
| 7,778,454 B2 | 8/2010 | Grasruck et al. | |
| 8,290,232 B2 * | 10/2012 | Liu et al. | 382/131 |
| 2004/0184574 A1 | 9/2004 | Wu et al. | |
| 2004/0264628 A1 | 12/2004 | Besson | |
| 2005/0084069 A1 | 4/2005 | Du et al. | |
| 2007/0217570 A1 * | 9/2007 | Grasruck et al. | 378/53 |
| 2007/0237288 A1 | 10/2007 | Tkaczyk et al. | |
| 2008/0013672 A1 * | 1/2008 | Krauss et al. | 378/4 |
| 2008/0037699 A1 | 2/2008 | Krauss | |

(Continued)

FOREIGN PATENT DOCUMENTS

CN        101028199 A     9/2007

OTHER PUBLICATIONS

Glantschnig et al. ("Mass fraction profiling based on x-ray tomography and its application to characterizing porous silica boules" Applied Optics, Mar. 15, 1987, vol. 26, No. 6).*

(Continued)

*Primary Examiner* — Seung C Sohn
*Assistant Examiner* — Jennifer Bennett
(74) *Attorney, Agent, or Firm* — Jenifer E. Haeckl

(57) ABSTRACT

A method for obtaining multi-material decomposition images of an object is presented. The method includes acquiring an image pair from a dual energy computed tomography scan of the imaged object. The method then includes selecting a material basis for multi-material decomposition of the image pair. The method further includes applying a physicochemical model for the material basis. Also, the method includes performing multi-material decomposition using at least one constraint imposed by the physicochemical model.

8 Claims, 9 Drawing Sheets

(56) References Cited

U.S. PATENT DOCUMENTS

2008/0253504 A1 10/2008 Proksa
2008/0253508 A1 10/2008 Krauss
2009/0086883 A1* 4/2009 Harer et al. .................. 378/4

OTHER PUBLICATIONS

Johnson et al.. "Material differentiation by dual energy CT: initial experience", Dec. 7, 2006, Springer-Verlag 2006.*

Heinzl, C.; Surface Extraction from Multi-Material Components for Metrology using Dual Energy CT; IEEE Transactions on Visualization and Computer Graphics; Nov.-Dec. 2007; pp. 1520-1527; vol. 13, Issue 6.

Mendonca et al., "Multi-Material Decomposition Using Dual-Energy CT", GE Global Research, One Research Circle, Niskayuna, NY 12309, 5 pages.

AAPM Annual Meeting Program, Medical Physics vol. 35 No. 6, Jun. 2008, pp. 2650.

* cited by examiner

US 9,036,879 B2

MULTI-MATERIAL DECOMPOSITION USING DUAL ENERGY COMPUTED TOMOGRAPHY

BACKGROUND OF THE INVENTION

The subject matter disclosed herein relates to computed tomography (CT) imaging systems and, in particular, to a multi-material decomposition method using dual energy x-ray sources for CT imaging systems.

Typically, in CT imaging systems, an x-ray source emits a fan-shaped or a cone-shaped x-ray beam toward a subject or object, such as a patient or a luggage item positioned on a support. The x-ray beam impinges on a detector assembly at the far side of the subject, comprising a plurality of detector modules, where the intensity of the x-ray beam detected is a function of the attenuation of the x-ray beam by the subject. In known "third generation" CT systems, the x-ray source and the detector assembly partially enclose the subject in a rotatable gantry structure. Data representing the intensity of the detected x-ray beam is collected across a range of gantry angles, and the data are ultimately processed to form an image.

A CT imaging system may be configured as an energy discriminating, a multi energy, and/or a dual energy CT imaging system. Dual energy CT imaging is an imaging procedure in which multiple scans are made of the same target under the same conditions at two different energy levels, or energy spectra, and is used to identify different materials in the target. For example, soft tissue and similar materials having a relatively low density typically attenuate incident x-rays to a lesser degree than does a relatively high density material, such as bone or an iodine contrast agent. It is appreciated in the relevant art that CT imaging performed at two imaging scans, one at a higher x-ray tube voltage level, such as 110 to 150 kVp, and another imaging scan performed at a lower x-ray tube voltage level, such as 60 to 80 kVp, provides more information about the materials being scanned than does a single-energy CT imaging scan.

Data obtained from a dual energy CT image scan can be used to reconstruct images using basis material decomposition computation processes. The generated images are representative of a pair of selected basis material densities. In addition to material density images, dual energy projection data can be used to produce a new image with x-ray attenuation coefficients equivalent to a selected monochromatic energy. Such a monochromatic image may include an image where the intensity values of image voxels are assigned as if a CT image were created by collecting projection data from the subject with a monochromatic x-ray beam.

In the medical imaging field, for example, dual energy CT scans may be performed at a relatively 'low energy' level of about 80 kVp, and at a relatively 'high energy' level of about 140 kVp, where the scans may be acquired "back-to-back" or interleaved. Special filters may be placed between the x-ray source and energy sensitive detectors such that different detector rows collect projections of different x-ray energy spectra.

The measurements may be obtained by: (i) scanning with two distinctive energy spectra; (ii) detecting photon energy according to energy deposition in the detector, and (iii) photon counting with multiple energy bins. In the absence of object scatter, the CT system can derive the information about object attenuation versus energy based on the signal from two or more regions of photon energy in the spectrum, for example, the low-energy and the high-energy portions of the incident x-ray spectrum. In medical CT, two physical processes dominate the x-ray attenuation: Compton scatter and the photoelectric effect. The detected signals from two energy regions usually provide sufficient information to resolve the energy dependence of the material being imaged. Furthermore, detected signals from the two energy regions provide sufficient information to determine the relative composition of an object composed of two materials.

Using the images obtained during these CT scans, one can generate basis material density images and monochromatic images, that is, images that represent the effect of performing a computed tomography scan with an ideal monochromatic tube source. Given a pair of material density images, it is possible to generate other basis material image pairs. For example, from a water and iodine image of the same anatomy, it is possible to generate a different pair of material density images such as calcium and gadolinium. Similarly, by using a pair of basis material images, one can generate a pair of monochromatic images, each at a specific x-ray energy. Similarly, one can obtain, from a pair of monochromatic images, a pair of basis material image pairs, or a pair of monochromatic images at different energies.

Conventional material basis decompositions utilize the concept that, in the energy region for medical CT, the x-ray attenuation of any given material can be represented by a proper density mix of two other materials, commonly denoted as "basis materials." The basis material deposition computing process produces two CT images, each representing the equivalent density of one of the basis materials. Since a material density is independent of x-ray photon energy, the two CT images are largely free of beam-hardening artifacts. An operator can choose the basis material to target a certain material of interest, for example, to enhance the image contrast.

Thus, dual-energy CT is an imaging modality that extends the capabilities of standard CT, and enables the estimation of the full linear attenuation curve for each voxel in the image volume, instead of a scalar image in Hounsfield units. As explained above, this is achieved by acquiring X-ray projections at two different energy spectra and, under careful calibration, reconstructing a material-decomposed image pair. Each co-registered voxel of this pair is a two-dimensional vector corresponding to an estimate, consistent with projection data, for the density of two pre-selected materials making up that voxel. Because the space of linear attenuation curves can be described as a two-dimensional manifold plus a residual difference which is too small to be measured under current CT technology, this decomposition procedure is essentially limited to the specification of only two materials.

The inventors herein have recognized a need for a method of producing computed tomography images of more than two pre-selected materials by multi-material decomposition.

BRIEF DESCRIPTION OF THE INVENTION

A method for obtaining multi-material decomposition images is disclosed, the method comprising the steps of: acquiring an image pair from a dual energy computed tomography scan of an imaged object; selecting a material basis for multi-material decomposition of the image pair; applying a physicochemical or mathematical model for the mix of materials in the basis; and performing multi-material decomposition using at least one constraint imposed by the physicochemical or mathematical model.

Other systems and/or methods according to the embodiments will become or are apparent to one with skill in the art upon review of the following drawings and detailed description. It is intended that all such additional systems and methods be within the scope of the present invention, and be protected by the accompanying claims.

DETAILED DESCRIPTION OF THE INVENTION

As noted above, conventional dual-energy CT scanner processing does not evaluate the composition of 'N≥3' materials in a material component mix, and is thus generally limited to a decomposition in only two materials (i.e., N=2). In an exemplary aspect of the disclosed method, the capabilities of the dual-energy CT scanner are expanded from producing a material-decomposed image pair to producing a material-decomposed image triplet. The image triplet is obtained by assuming that the various mixtures of substances and tissue types found in the human body have physicochemical properties substantially equivalent to those of what is herein denoted as an 'ideal material solution.' This can also be done by using a model for the excess free energy of the mixture. Using this equivalence provides a model for the density of an imaged material mixture, where the model complements the image information provided by the conventional CT data. Under this model, the mass attenuation curve of a particular voxel in a CT image is estimated, and a material-decomposed image triplet is derived (i.e., N=3). In another exemplary aspect of the disclosed method, more than three pre-selected materials can be decomposed by regularizing an otherwise under-constrained solution of a system of equations with a suitable function, and solving the resulting optimization problem. The disclosed method may also use pre-computed lookup tables for faster decomposition.

Figure 1:
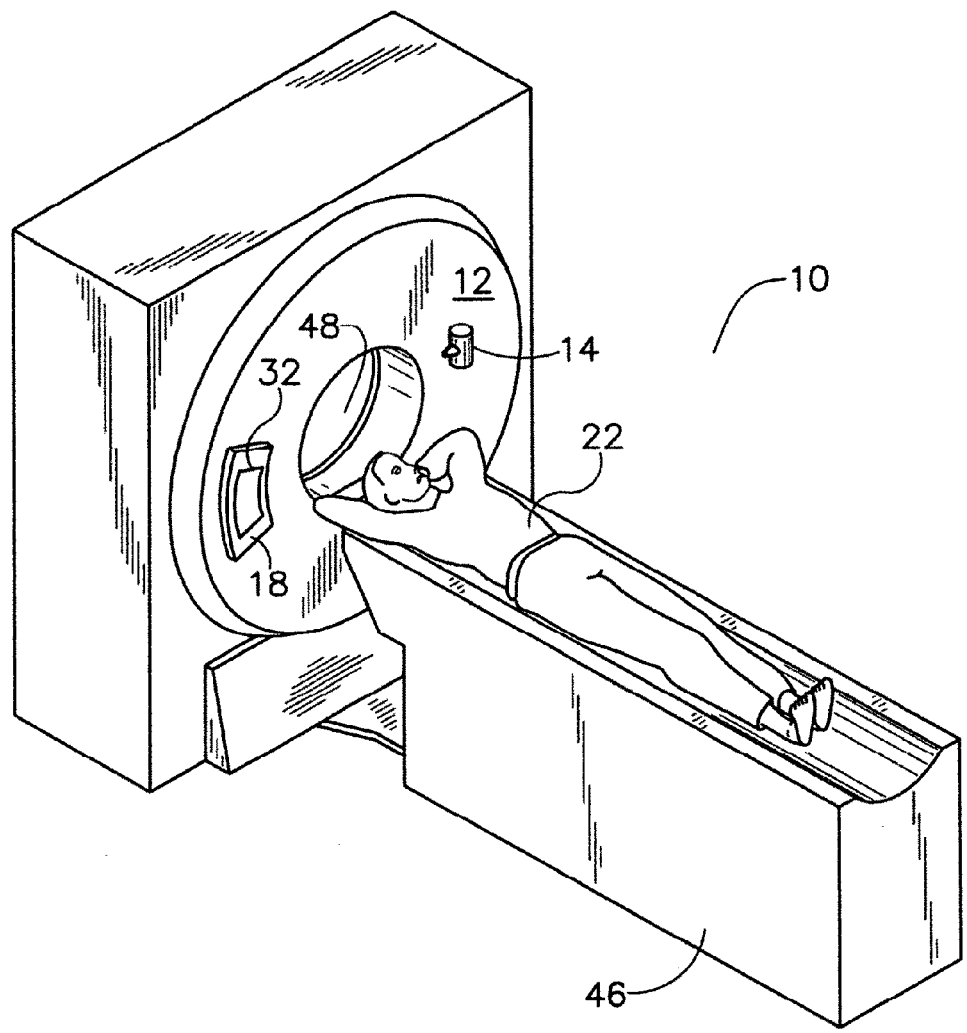
FIG. 1 is an isometric diagrammatical view of a CT imaging system, in accordance with the prior art.
Figure 2:
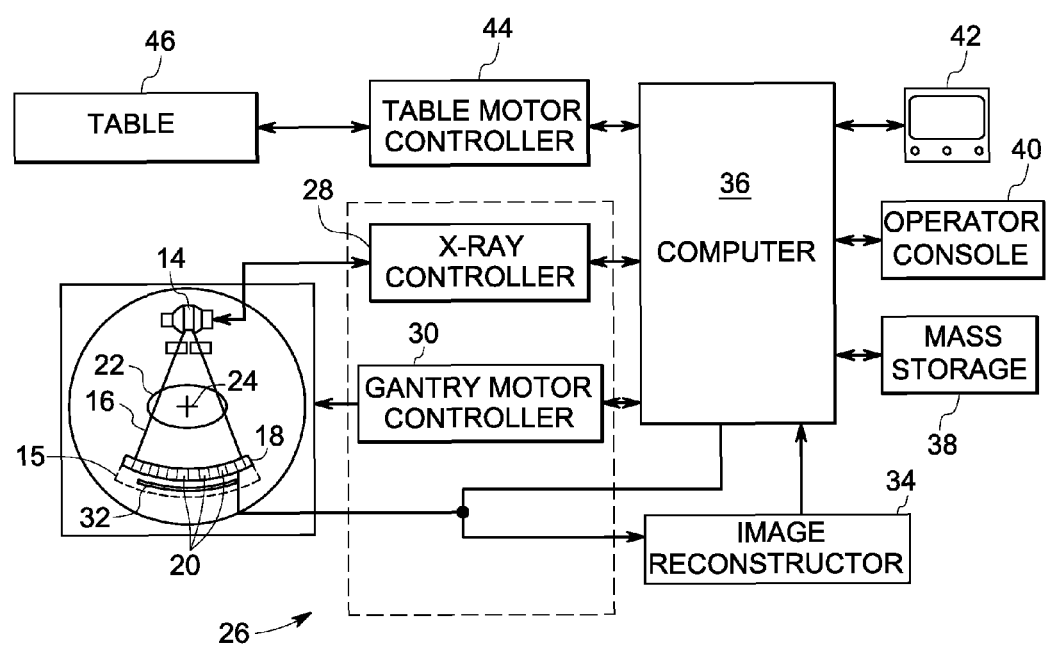
FIG. 2 is a functional block diagram of the CT imaging system of FIG. 1.

There is shown in the isometric diagrammatical illustration of FIG. 1 a dual-energy CT imaging system 10 configured to perform computed tomography imaging by means of photon counting and energy discrimination of x-rays at high flux rates, as is known in the relevant art. Imaging may be performed by, for example, a CT number difference decomposition, a basis material decomposition, a Compton and photoelectric decomposition, or a logarithmic subtraction decomposition. The dual-energy CT imaging system 10 comprises a gantry 12, with a collimator assembly 18, a data acquisition system 32, and an x-ray source 14 disposed on the gantry 12 as shown. A table 46 serves to move all or part of a patient 22 through a gantry opening 48 in the gantry 12.

The x-ray source 14 projects a beam of x-rays 16 through the patient 22 onto a plurality of detector modules 20 in a detector assembly which includes the collimator assembly 18 and the data acquisition system 32. In a typical embodiment, the detector assembly may comprise sixty four rows of voxel elements to enable sixty four simultaneous "slices of data" to be collected with each rotation of the gantry 12.

The plurality of detector modules 20 sense the projected x-rays that pass through the patient 22, and the data acquisition system 32 converts the data to digital signals for subsequent processing. Each detector module 20 produces an analog electrical signal that represents the intensity of an attenuated x-ray beam after it has passed through the patient 22. During a scan to acquire x-ray projection data, the gantry 12 rotates about a center of rotation 24 along with the x-ray source 14 and the detector assembly 15.

The rotation of the gantry 12 and the operation of the x-ray source 14 are controlled by a control mechanism 26. The control mechanism 26 includes an x-ray generator 28 that provides power and timing signals to the x-ray source 14, and a gantry motor controller 30 that controls the rotational speed and position of the gantry 12. An image reconstructor 34 receives sampled and digitized x-ray data from the data acquisition system 32 and performs high speed reconstruction. The reconstructed image is applied as an input to a computer 36 which stores the image in a mass storage device 38.

The computer 36 also receives commands and scanning parameters input from an operator console 40. An associated image display 42, such as a cathode ray tube, allows an operator to observe the reconstructed image and other data from the computer 36. The commands and scanning parameters are used by the computer 36 to provide control signals and information to the data acquisition system 32, the x-ray generator 28, and the gantry motor controller 30. In addition, the computer 36 operates a table motor controller 44 which controls the motorized table 46.

In conventional CT scanner processing, the data produced by the conventional system is an estimate of the linear attenuation curve of the imaged object at each voxel of the CT imaged volume of interest. A linear attenuation curve is a function that allows for the computation of the fraction of photons that travel undisturbed a fixed length of material at a certain density as a function of the energy of such photons. For example, the linear attenuation coefficient of liquid water is 0.294 cm$^{-1}$ for x-ray photon incident energy of 100 keV. That is, about 74.5% ($e^{-0.294}$) of the total number of incident photons with energy of 100 keV will be left undisturbed when traveling through 1.0 cm of liquid water having density of 1.00 g/cm$^3$. For photons with energy of 200 keV, the linear attenuation coefficient of liquid water is 0.243 cm$^{-1}$ and 78.4% ($e^{-0.243}$) of the total number of incident photons with energy of 200 keV will be left undisturbed when traveling though 1.0 cm of liquid water. In comparison, only 0.007% of photons with energy of 100 keV and 16.46% of photons with energy of 200 keV will travel undisturbed through 1.0 cm of iodine with a density of 4.93 g/cm$^3$ and a linear attenuation coefficient of 1.94 cm$^{-1}$.

The linear attenuation curve of substantially any material at substantially any density can be uniquely described as a weighted sum of the linear attenuation curves of two other materials. From a mathematical standpoint, the choice of materials (i.e., the material basis) is largely arbitrary but in practical applications the materials found in the imaged pairs are preferred. For example, in a clinical application the operator will generally select materials found in the human body, such as water, fat, and bone. Furthermore, for a given material basis and attenuation curve, the weighting coefficients may be uniquely defined such that the weighted sum of linear attenuation curves is equal to the original attenuation curve. Each weighting coefficient multiplying a linear attenuation curve of a given material can also be multiplied by the nominal density of the material, and the result is a material-density image pair, as shown in FIGS. 3-4.

Figure 3:
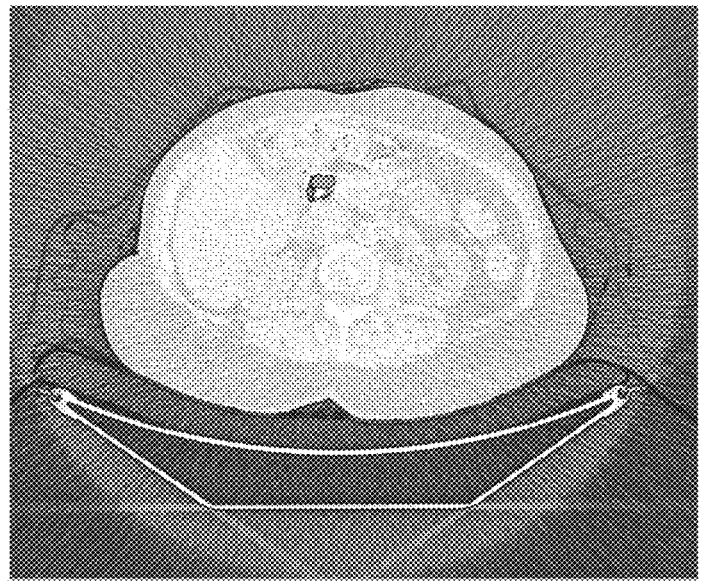
FIG. 3 is a water-component image from a decomposition in two materials, as may be provided by the CT imaging system of FIG. 1 operating in a dual energy mode.
Figure 4:
FIG. 4 is an iodine-component image from a decomposition in two materials, as may be provided by the CT imaging system of FIG. 1 operating in a dual energy mode.
Figure 5:
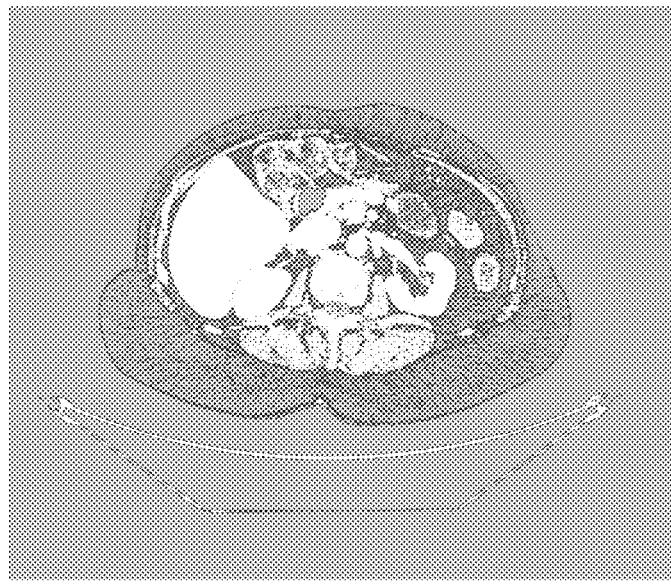
FIG. 5 is a monochromatic image showing attenuation at 70 keV, from a decomposition into two monochromatic images, as may be obtained by the CT imaging system of FIG. 1 operating in a dual energy mode.
Figure 6:
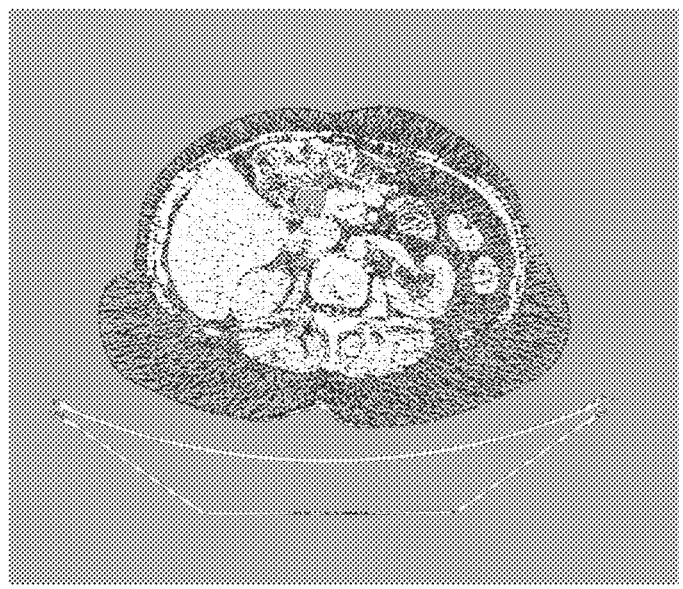
FIG. 6 is a monochromatic image showing attenuation at 140 keV, from a decomposition into two monochromatic images, as may be obtained by the CT imaging system of FIG. 1 operating in a dual energy mode.

Thus, the computer 36 may decompose a material-density image pair onto the image display 42, such as a water component image 52, shown in FIG. 3, and an iodine component image 54, shown in FIG. 4. In the iodine component image 54, the air region outside the body has resulted in an iodine-equivalent density comparable to that found inside the body. Alternatively, the computer 36 may decompose an energy image pair, such as a first monochromatic image 56 showing attenuation at 70 keV, shown in FIG. 5, and a second monochromatic image 58 showing attenuation at 140 keV, shown in FIG. 6. In the disclosed multi-material decomposition method, which can best be described with reference to a flow diagram 60 shown in FIG. 7, the dual-energy CT imaging system 10 acquires either a material-density image pair or an energy image pair from x-ray projections of two energy spectra, in step 62.

From a mathematical standpoint, there is no constraint on the values of the weighting coefficients necessary to represent a given linear attenuation cure through a weighted sum. Such weighting coefficients could, in principle, even be negative. However, once a negative coefficient is multiplied by a nominal density to produce a density image, the user of the images is left with the problem of interpreting the meaning of the negative density values that result. It is also possible for the weight associated with the linear attenuation curve to assume a value greater than one, and producing a density value greater that the nominal density of the corresponding material. Accordingly, the capabilities of the dual-energy CT scanner 10 can be expanded from producing only a material-decomposed image pair to also producing a material-decomposed image pair more amenable to physical interpretation by enforcing the constraint that the weighting coefficients multiplying a linear attenuation curve must be non-negative and must be less than or equal to one.

In accordance with the disclosed method, the linear attenuation curve is divided by an actual (not nominal) material density to obtain a mass attenuation curve. The resulting mass attenuation curve is density independent, but is material dependent inasmuch as the mass attenuation curve can be represented as the weighted sum of the curves of other materials, similar to the linear attenuation curve. However, the mass attenuation curve has the additional attribute that the weighting coefficients have a well-defined physical meaning as mass fractions of the constituent materials in the material mix. As can be appreciated, the sum of the weighting coefficients in the mass attenuation curve is unity.

As explained in greater detail below, the weighting coefficients $\alpha$ in a weighted sum of linear attenuation coefficients can be related to the weighting coefficients $\beta$ in a weighted sum of mass attenuation coefficients through a model for how the materials in the material basis mix. For example, by assuming an ideal material solution, the constraint that the weighting coefficients $\beta$ sum to unity can also be imposed on the weighting coefficients $\alpha$. This allows for expressing the linear attenuation curve of a given material as a sum of three linear attenuation curves, instead of the conventional two curves. As understood in the relevant art, decomposition into two materials yields a unique pair of weighting coefficients, but without further constraints, the triplet material decomposition produces an infinite set of triplets of weighting coefficients. The set of triplets is one-dimensional, as each triplet in the set can be uniquely associated to a parameter. For any given choice of three materials, this parameter can be interpreted as a 'dial' that allows a user to select a triplet of weighting coefficients in the set. The corresponding triplet of weighting coefficients results in the same weighted sum of linear attenuation curves. The weighted sum is satisfied by an arbitrary choice of triplets in the set of triplets. However, if an external constraint is provided, only one 'dial setting' will yield a triplet that satisfies the constraint that the weighting coefficients $\alpha$ sum to unity. A relation between $\alpha$ and $\beta$ can be established if a model for the density of the mix of materials in a given material triplet is available.

In accordance with the disclosed method, physicochemical models can be used to establish relationships between the densities and quantities of given materials and the density of a mix of the given materials, so as to provide for triple material decomposition. One of the physicochemical models used may be that of an 'ideal solution.' The disclosed method works from the presumption that the mixture of component materials form an ideal solution, and thus that the volume of the ideal solution, at a given temperature and pressure, is equal to the volume of the component parts of the mix at the same temperature and pressure. Accordingly, it can be shown that the weighting coefficients $\alpha$ in the decomposition of a linear attenuation curve as the weighted sum of linear attenuation curves of other materials have a straightforward physical interpretation—that the weighting coefficients are the volume fractions of the component materials in the material mix.

Referring again to FIG. 7, a material basis is specified having (N≥3) material components, in step 64. The particular material components specified for the material basis may be selected from among the substances and tissue types identified as appearing in the material-density image pair or the energy image pair. In an exemplary embodiment, a selection of fat, bone, and blood may be made via the operator console 40.

It is known in the practice of dual-energy computed tomography that the linear attenuation coefficient of a given material is dependent on: (i) the energy E of the imaging x-rays, (ii) the mass density of the imaged materials, and (iii) the effective atomic number of the imaged materials. The linear attenuation coefficient $\mu_L(E)$ for a given material can be expressed as the sum $$\mu_L(E) = \sum_i^N \alpha_i \mu_{L,i}(E), \quad (1)$$

where $\alpha_i$, i=1,2, ... N are energy-independent constants and $\mu_{L,i}(E)$, i=1,2, ... N are the linear attenuation curves of N arbitrarily pre-selected materials. For materials found in the human body and within the detection range of x-ray energies typically used in medical imaging, the linear attenuation coefficient $\mu_L(E)$ can be represented by a linear combination of component materials, commonly denoted as a 'material basis.' Thus, given a measurement of $\mu_L(E)$ at two distinct energy levels, for which $\mu_{L,1}$ and $\mu_{L,2}$ are known, unique solutions can be found for $\alpha_1$ and $\alpha_2$ so as to provide a material basis for two component materials. However, a conventional dual-energy CT scanner cannot decompose into a material basis having three or more component materials.

By introducing an additional constraint, the disclosed method provides for decomposition of a third component material. The relation in equation (1) can be expressed in terms of a 'mass attenuation coefficient' $\mu_M(E)$ that is related to the linear attenuation coefficient by the expression $$\mu_M(E) = \frac{\mu_L(E)}{\rho} \quad (2)$$

where $\rho$ is the mass density of a given component material M, as the component material M is disposed within an imaged aggregate of component materials. Equation (1) can be rewritten as:

$$\mu_M(E) = \sum_i^N \beta_i \mu_{M,i}(E), \quad (3)$$

where Equation (3) has the added constraints:

$$0 \leq \beta_i \leq 1; \text{ for } i = 1, 2, \ldots, N \quad (4a)$$

$$\sum_i^N \beta_i = 1 \quad (4b)$$

The coefficients $\beta_i$ are the mass fractions of each component material in the imaged aggregate of component materials. By establishing a relationship between the energy-independent coefficients $\alpha_i$ in Equation (1) and the mass fraction coefficients $\beta_i$ in Equation (2), an additional constraint is provided that provides for a further decomposition by the dual-energy CT scanner.

Figure 7:
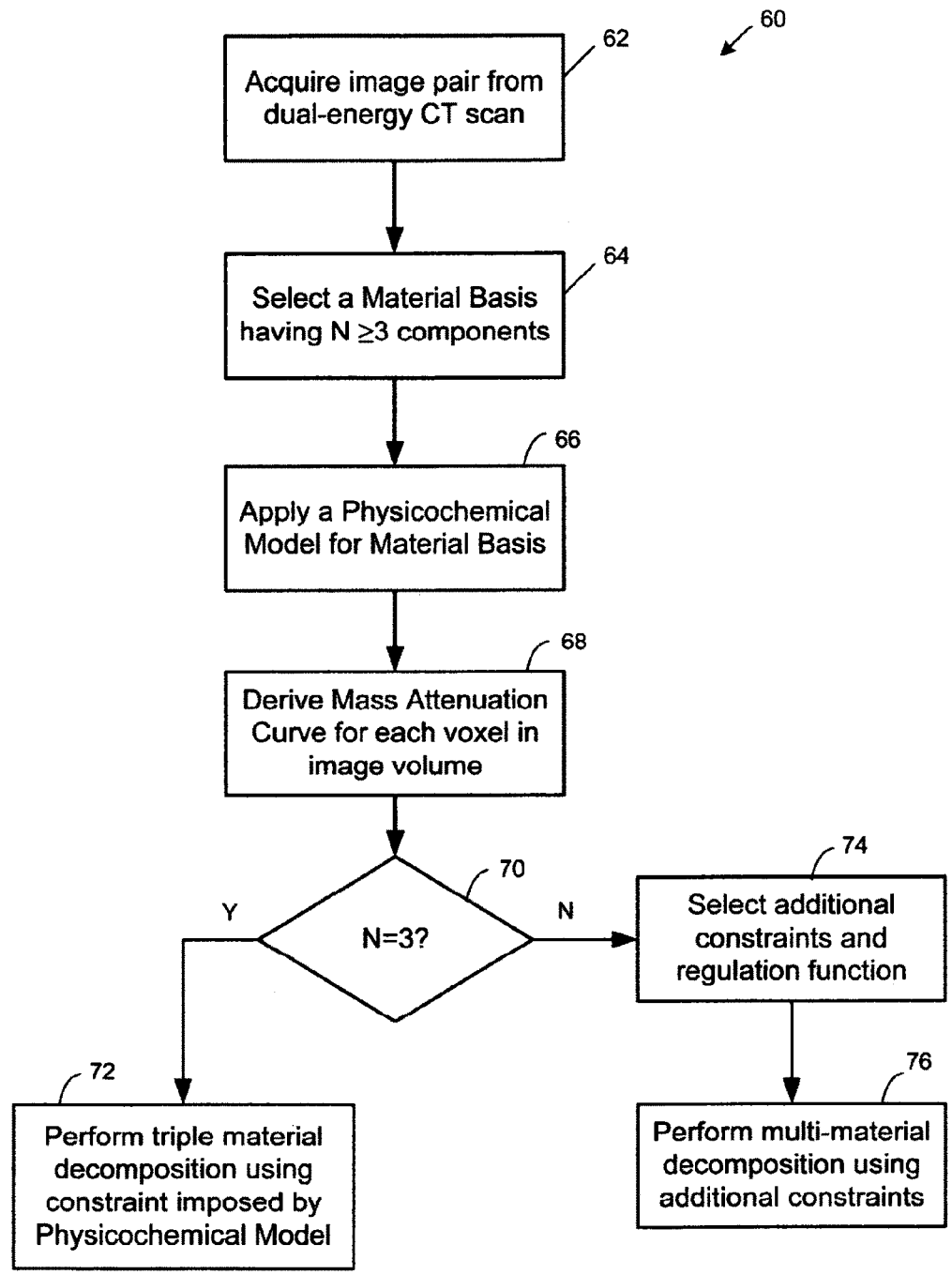
FIG. 7 is a flow diagram illustrating the operation of a dual-energy CT imaging system functioning to provide multi-material decomposition, in accordance with the disclosed method.

Referring again to the flow chart 60 of FIG. 7, a physicochemical model, or properties model, for relevant properties (density, volume, etc) of the selected material mix is applied, in step 66. The disclosed process uses a physicochemical model to determine the density of a material mix, bringing in one more constraints to the two constraints already available via the dual-energy image pair. This immediately allows for the decomposition of the images into a material triplet. One model for the density of the imaged aggregate of component materials can be derived by assuming that the component materials form an 'ideal solution,' that is, a component mixture having a volume at a given temperature and pressure essentially equal to the sum of the volumes of the individual component parts at the same temperature and pressure. It can be shown that this leads to the following constraints:

$$0 \leq \alpha_i \leq 1; \text{ for } i = 1, 2, \ldots, N \quad (5a)$$

$$\sum_i^N \alpha_i = 1 \quad (5b)$$

where $$\alpha_i = \frac{V_i}{\sum_{j=1}^N V_j} \quad (6)$$

That is, a well-posed, triple-material decomposition can be obtained from a dual-energy CT scanner image pair by specifying that the component materials in the aggregate mixture of imaged materials comprise an ideal solution.

A derivation or estimate is made of the mass attenuation curve for each voxel in the image volume, at step 68. A determination is made, at decision block 70, whether three material basis components are being used (i.e., N=3). If the response is "yes," operation proceeds to step 72 at which the triple-material decomposition is solved. If, at decision block 70, the response is "no," a regularization function is selected, at step 74, to constrain the otherwise ill-posed solution of the multi-material decomposition problem. The multi-material decomposition is solved under the additional physicochemical constraints, at step 76, as described in greater detail below.

Figure 8:
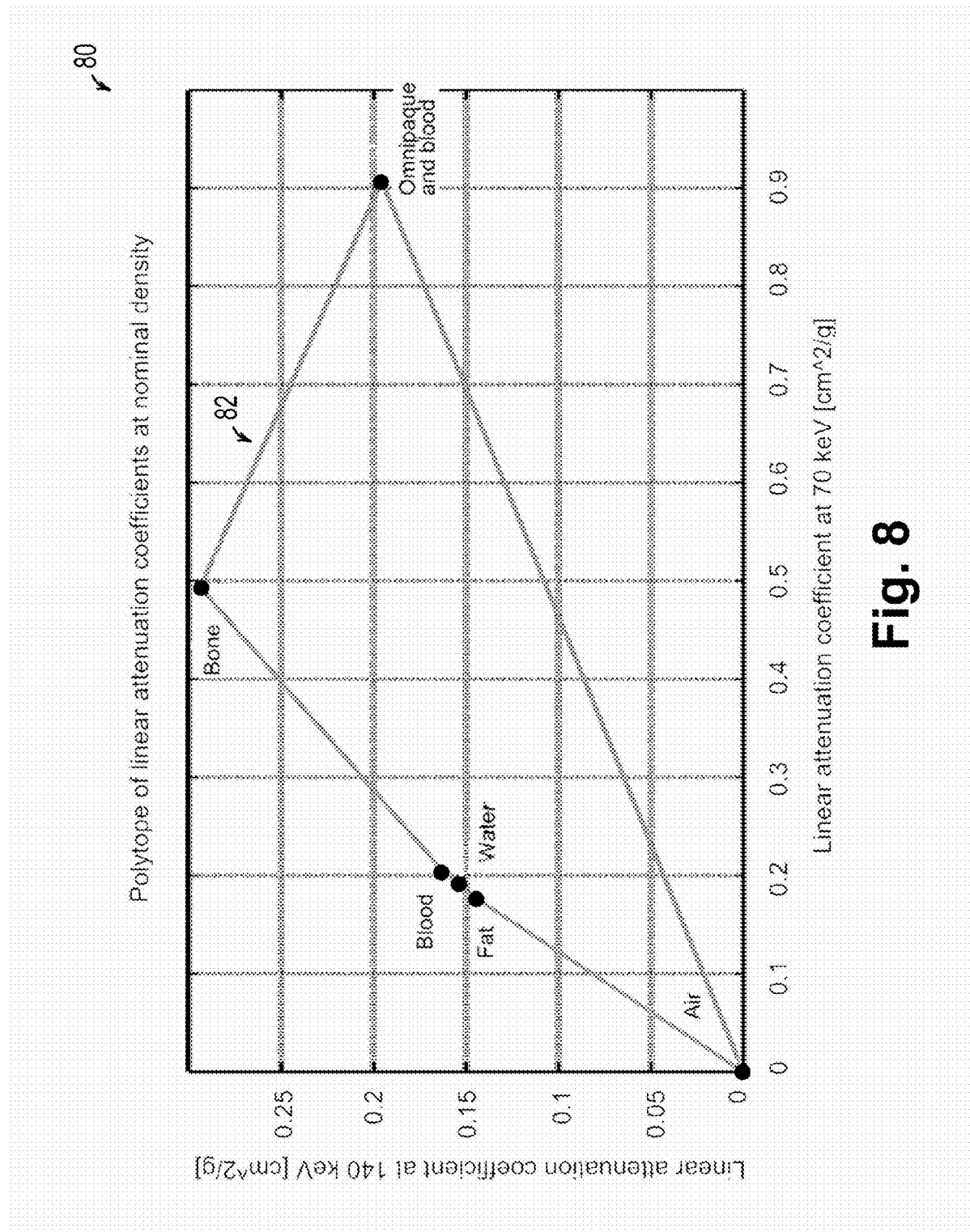
FIG. 8 is a graph illustrating a convex polytope of linear attenuation coefficients at nominal density.

By way of explanation for step 72, because of the constraints in equations (5a) and (5b), the energy-independent constants $\alpha_i$ in Equation (1) can be viewed as weights in a combination of the linear attenuation coefficients of the respective component materials, in the imaged aggregate of component materials, at the nominal material densities. It can be appreciated by one skilled in the art that material's linear attenuation properties at two arbitrary, but fixed, energy levels $E_1$ and $E_2$ can be represented as a point in a two-dimensional space having coordinates $\mu_L = (\mu_L(E_1), \mu_L(E_2)) E_1$. This may be exemplified by a graph 80, shown in FIG. 8. The graph 80 shows dual-energy linear attenuation coefficient values of N arbitrary materials plotted along orthogonal axes. When the material mix in the human body is modeled as an ideal solution, $\mu_L$ is inside the convex hull $\boldsymbol{H}$ of the set $\{\mu_{L,i}, i=1,2,\ldots,N\}$. That is, the linear attenuation coefficients for a given energy pair fall within the convex hull 82 of the linear attenuation coefficients of the imaged aggregate of component materials.

However, for N>3, the condition that $\mu_L \in \boldsymbol{H}$ serves to constrain only the range of the energy-independent coefficients $\alpha_i$, and is not adequate to fully specify the values of the coefficients $\alpha_i$. In this case, a unique solution can be obtained by adding the farther constraint that a suitable function $f$ of the vector $\alpha = (\alpha_1, \alpha_2, \ldots, \alpha_N)$ is minimal, and an N-material decomposition for N>3 can be obtained by solving the optimization problem given by:

$$\alpha^* = \min_\alpha f(\alpha) \quad (7)$$

and by meeting the conditions of Equations 1, 5a, and 5b, above.

In accordance with the disclosed method, multi-material (N>3) decomposition is achieved through the introduction of further constraints on the weights of the weighted sum of the linear attenuation curves. Such further constraints include, for example, data-fidelity constraints, constraints based on the spatial dependency of voxels, and constraints derived from prior knowledge of the operator.

For N>3, the disclosed process can be further expanded by introducing a regularization function to the otherwise unconstrained solution of the N-material decomposition problem. The regularization function for determining the multiple material contributions, at step 76, can be selected depending on the anatomy that is being looked at based on a priori knowledge of the common characteristics of the material make-up of the relevant anatomy. For example, if the operator is looking at the liver, the regularization function may be tailored to favor water, iohexol, and blood over bone.

In an exemplary embodiment of the disclosed method, step 74 can be carried out off-line to create a lookup table for interactive visualization of the results. Multiple look up tables may be pre-generated with decompositions across different sets of materials. The particular table to be used for a decomposition can be chosen based on the anatomy/region of interest based on the a priori knowledge of the material make-up of that region. Moreover, the lookup tables may be generated 'on the fly' based on user input. The operator could specify the materials of interest based on some ambiguity to be resolved, or else interact with a scatter plot feature and to define the convex hull manually.

Figure 9:
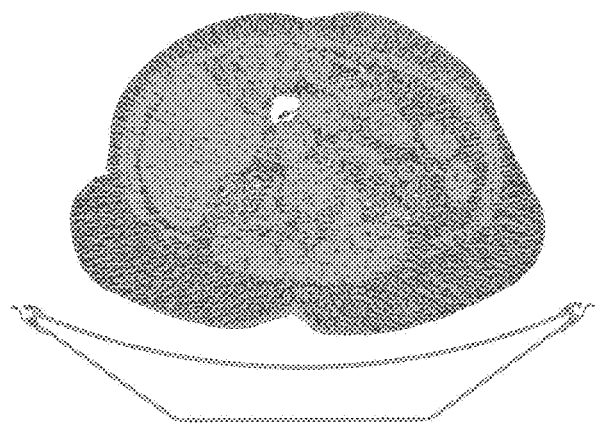
FIG. 9 is a an air-component image from a multi-material decomposition, obtained in accordance with the disclosed method.
Figure 10:
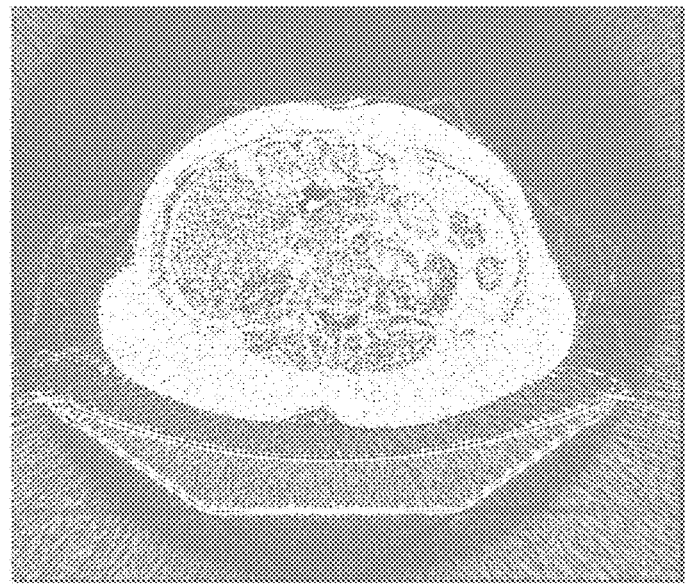
FIG. 10 is a fat-component image obtained from the multi-material decomposition process used to produce the image of FIG. 9.
Figure 11:
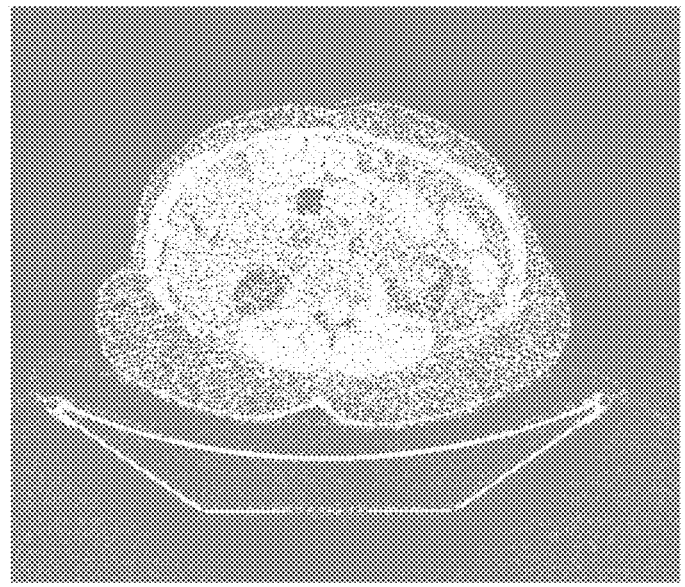
FIG. 11 is a blood-component image obtained from the multi-material decomposition process used to produce the image of FIG. 9.
Figure 12:
FIG. 12 is a bone-component image obtained from the multi-material decomposition process used to produce the image of FIG. 9.
Figure 13:
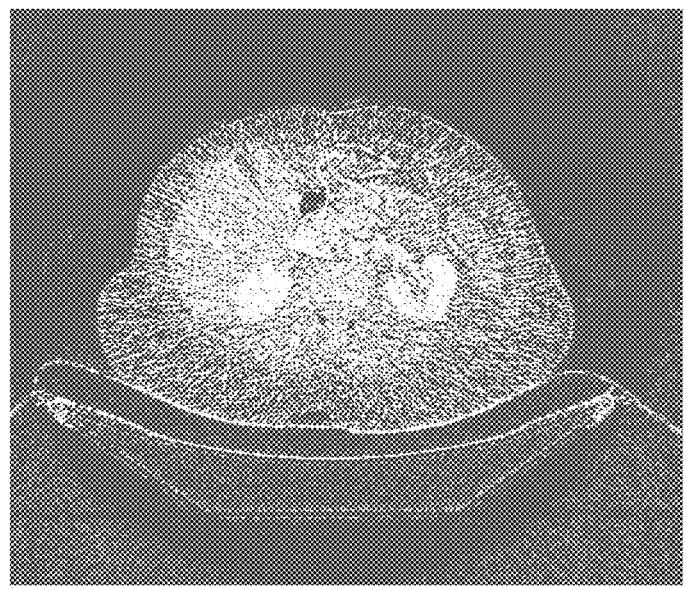
FIG. 13 is an Omnipaque-component image obtained from the multi-material decomposition process used to produce the image of FIG. 9.

Example of the multi-material decomposition performed at step 76 of flow chart 60 are provided in the images of FIGS. 9-13. FIG. 9 is an air component image obtained with multi-material decomposition. FIG. 10 is a fat component image, FIG. 11 is a blood component image, FIG. 12 is a bone component image, and FIG. 13 is an Omnipaque-component image. The images resulting from this type of multi-decomposition have fractional voxel values that represent the contribution from a particular material. These images can be leveraged in a number of ways, including without limitation, the following examples:

- A weighting function on a monochromatic image to represent the attenuation due to a particular material—this would include the multiplication of a particular monochromatic image by the volume fraction image;
- AIR image can be used to identify contours of the body and interior vacuous regions (e.g., used for lung segmentation by counting the number of crossings in and out of this AIR region);
- Segmentation based on threshold volume fraction (e.g., bone is the region that is >90% volume fraction on the bone image);
- Providing a color overlay on top of standard images showing color intensity based on volume fraction image;
- Inputting to a generalized segmentation engine—where one or more volume fraction images that result from the multi-material decomposition procedure are used in a material segmentation process;
- Generating a virtual non-contrast image by replacing volume fraction associated with the Omnipaque with another component such as blood; and
- Liver fat quantification, or general fat quantification, by using a fat-volume fraction image.

The plurality of detector modules 20 sense the projected x-rays that pass through the patient 22, and the data acquisition system 32 converts the data to digital signals for subsequent processing. Each detector module 20 in a conventional system produces an analog electrical signal that represents the intensity of an attenuated x-ray beam after it has passed through the patient 22. During a scan to acquire x-ray projection data, the gantry 12 rotates about a center of rotation 24 along with the x-ray source 14 and the detector assembly 15.

The above-described methods can be embodied in the form of computer program code containing instructions embodied in one or more tangible media, such as floppy diskettes and other magnetic storage media, CD ROMs and other optical storage media, flash memory and other solid-state storage devices, hard drives, or any other computer-readable storage medium, wherein, when the computer program code is loaded into and executed by a computer, the computer becomes an apparatus for practicing the disclosed method.

While the invention is described with reference to exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for obtaining multi-material decomposition images, said method comprising the steps of:
    acquiring an image pair from a dual energy computed tomography scan of an imaged object;
    selecting a material basis for multi-material decomposition of said image pair;
    at each image location in said image pair, applying a physicochemical model for said material basis to produce a triple-material decomposition;
    determining a plurality of decomposition coefficients associated with the triple-material decomposition; and
    selecting a material triplet corresponding to the triple-material decomposition when the decomposition coefficients comprise a non-negative value.

2. The method of claim 1 further wherein said image pair comprises one of a material-density image pair and an energy image pair.

3. The method of claim 1 further comprising the step of deriving a mass attenuation curve from a linear attenuation curve for each image location in said image pair.

4. The method of claim 3 wherein said step of deriving comprises multiplication by at least one weighting coefficient, said weighting coefficient having a value lying between zero and one.

5. The method of claim 1 wherein said physicochemical model comprises an ideal solution, said ideal solution having a volume, at a given temperature and pressure, equal to the volume of component materials in the physicochemical mix at the same temperature and pressure.

6. The method of claim 1, wherein the material triplet is selected from at least three body material components found in said image pair.

7. The method of claim 1, wherein the material triplet is selected by performing a regularization function to the triple-material decomposition.

8. A non-transitory computer program product for performing multi-material decomposition on computed tomography images, said non-transitory computer program product comprising:
- a computer-readable medium for storing computer code for execution by a computer;
- a first program code for selecting a material basis for multi-material decomposition of an image pair acquired from a computed tomography scan;
- a second program code for applying a physicochemical model for said material basis to produce a triple-material decomposition at each image location in said image pair; and
- a third program code for determining a plurality of decomposition coefficients associated with the triple-material decomposition and selecting a material triplet corresponding to the triple-material decomposition when the decomposition coefficients comprise a non-negative value;
- wherein said first, second, and third program codes are stored on said computer-readable medium.

* * * * *